United States Patent
Deaven et al.

(10) Patent No.: US 7,623,696 B2
(45) Date of Patent: Nov. 24, 2009

(54) METHOD AND APPARATUS FOR REMOTE PROCESSING OF IMAGE DATA

(75) Inventors: David Matthew Deaven, Delafield, WI (US); Girish Kumar Muralidharan, Pewaukee, WI (US)

(73) Assignee: GE Medical Systems, Inc, Waukesha, WI (US)

( * ) Notice: Subject to any disclaimer, the term of this patent is extended or adjusted under 35 U.S.C. 154(b) by 0 days.

(21) Appl. No.: 11/970,417

(22) Filed: Jan. 7, 2008

(65) Prior Publication Data
US 2008/0104174 A1     May 1, 2008

Related U.S. Application Data

(63) Continuation of application No. 10/722,725, filed on Nov. 25, 2003, now Pat. No. 7,327,864.

(51) Int. Cl.
*G06K 9/00* (2006.01)
*A61B 6/04* (2006.01)

(52) U.S. Cl. .................... 382/128; 382/154; 378/37

(58) Field of Classification Search ............ 382/100, 382/128, 129, 130, 131, 134, 155, 156, 159, 382/181, 168, 193, 203, 209, 224, 274, 276, 382/294, 291, 305, 318, 272, 132, 133; 707/3; 378/37; 435/6; 713/163; 715/751; 714/43
See application file for complete search history.

(56) References Cited

U.S. PATENT DOCUMENTS

| 6,195,091 | B1 * | 2/2001 | Harple et al. ............... 715/751 |
| 6,665,820 | B1 * | 12/2003 | Frowein et al. ............... 714/43 |
| 6,772,335 | B2 * | 8/2004 | Curtis et al. ................ 713/163 |
| 6,785,410 | B2 | 8/2004 | Vining et al. |
| 6,891,920 | B1 * | 5/2005 | Minyard et al. ............... 378/37 |
| 7,026,121 | B1 * | 4/2006 | Wohlgemuth et al. .......... 435/6 |
| 7,047,235 | B2 * | 5/2006 | Yang et al. ..................... 707/3 |

\* cited by examiner

*Primary Examiner*—Seyed Azarian
(74) *Attorney, Agent, or Firm*—Fletcher Yoder

(57) ABSTRACT

A technique is provided for collaboratively processing and/or analyzing a set of image data. The technique provides for the initiation of a collaborative session by an application server. One or more collaborative workstations may join the collaborative session, providing common access to an image data set and to tools for processing and/or viewing the image data set. Operators at the collaborative workstations and/or the application server may thereby simultaneously access, process, and/or analyze the image data set. Communication between the operators via the network supporting the collaborative session may also be provided.

13 Claims, 2 Drawing Sheets

METHOD AND APPARATUS FOR REMOTE PROCESSING OF IMAGE DATA

CROSS REFERENCE TO RELATED APPLICATIONS

This application is a Continuation of U.S. patent application Ser. No. 10/722,725, entitled "Method and Apparatus for Remote Processing of Image Data", filed Nov. 25, 2003, which is herein incorporated by reference in its entirety for all purposes.

BACKGROUND OF THE INVENTION

The present invention relates generally to the remote processing and/or review of image data. More specifically, the present invention relates to the remote processing and/or review of image data acquired by non-invasive imaging systems, such as those used in medical imaging or for security screening.

A wide variety of medical imaging technologies, such as digital X-ray, tomosynthesis, X-ray mammography, computed tomography (CT), positron emission tomography (PET), electron beam tomography (EBT), magnetic resonance imaging (MRI), and so forth, have become commonplace at both large and small medical facilities. These imaging technologies are typically capable of non-invasively acquiring image data of an anatomic region of interest. The image data may typically be processed to generate two-dimensional images or three-dimensional models representing the surface or interior features of the anatomic region of interest.

Typically, a referring physician, who may have little or no training in analyzing or reading radiological images, will refer a patient for diagnostic imaging. A technologist may perform the image acquisition of the patient using the desired imaging technology. The technologist may then process the image data to generate the two-dimensional images and/or three-dimensional models based upon the acquired image data. Due to the relative scarcity of trained technologists and the proliferation of imaging technologies, however, the time or expertise for proper processing may be at a premium. It may therefore be desirable to find techniques to facilitate or share the processing of the image data.

The radiologist, who is typically specialized in the imaging technology and/or the anatomical region of interest, analyzes or "reads" the processed image data. The radiologist typically reads the image data at a review workstation, which may or may not be near the imaging system and/or the referring physician. The radiologist may dictate plain, text descriptions of her diagnostic conclusions at the time she reads the image data. The dictated comments may then be provided to the referring physician, typically with the image data to which they relate, who may then counsel the patient regarding any diagnostic findings.

As may be expected, the patient outcome may depend on the speed and quality of the diagnosis and on the communication of the diagnosis and associated factors from the radiologist to the referring physician and to the patient. For example, in routine situations, such as patient office visits, the ability of the referring physician to communicate the diagnosis to the patient may be essential for behavior modification which may improve the patient's health. The quality of the diagnosis and the speed and effectiveness with which it is communicated to the referring physician is therefore an important part of the imaging process. Facilitating or improving the diagnostic process and/or the communication process may therefore be important goals in patient treatment.

BRIEF DESCRIPTION OF THE INVENTION

The present invention relates generally to providing for the remote processing and/or review of imaging data. A collaborative imaging system is provided by which a remote technologist may perform all or part of the post-processing of a set of image data, allowing the local technologist to perform examinations more rapidly. Alternatively, the collaborative imaging system may allow a referring physician and radiologist to review a processed set of image data in a collaborative manner, such as using a common desktop or screen, and with real-time, dynamic communications. Similarly, other radiologists, technologists, or other experts may collaboratively view, analyze, or process the image data sets as desired, allowing the expertise of multiple radiologists and/or technologists to be applied to an image data set in a concurrent or collaborative manner.

In accordance with one aspect of the present technique, a method for collaboratively handling an image data set is provided. In the present technique, a collaborative session is initiated on an application server connected to a network. One or more collaborative workstations on the network are joined to the collaborative session, such that the one or more collaborative workstations and the application server comprise participating nodes of the collaborative session. One or more routines stored on the application server are provided to the participating nodes. The one or more routines are useful for at least one of processing and analyzing an image data set. Systems and computer programs that afford functionality of the type defined by this method are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
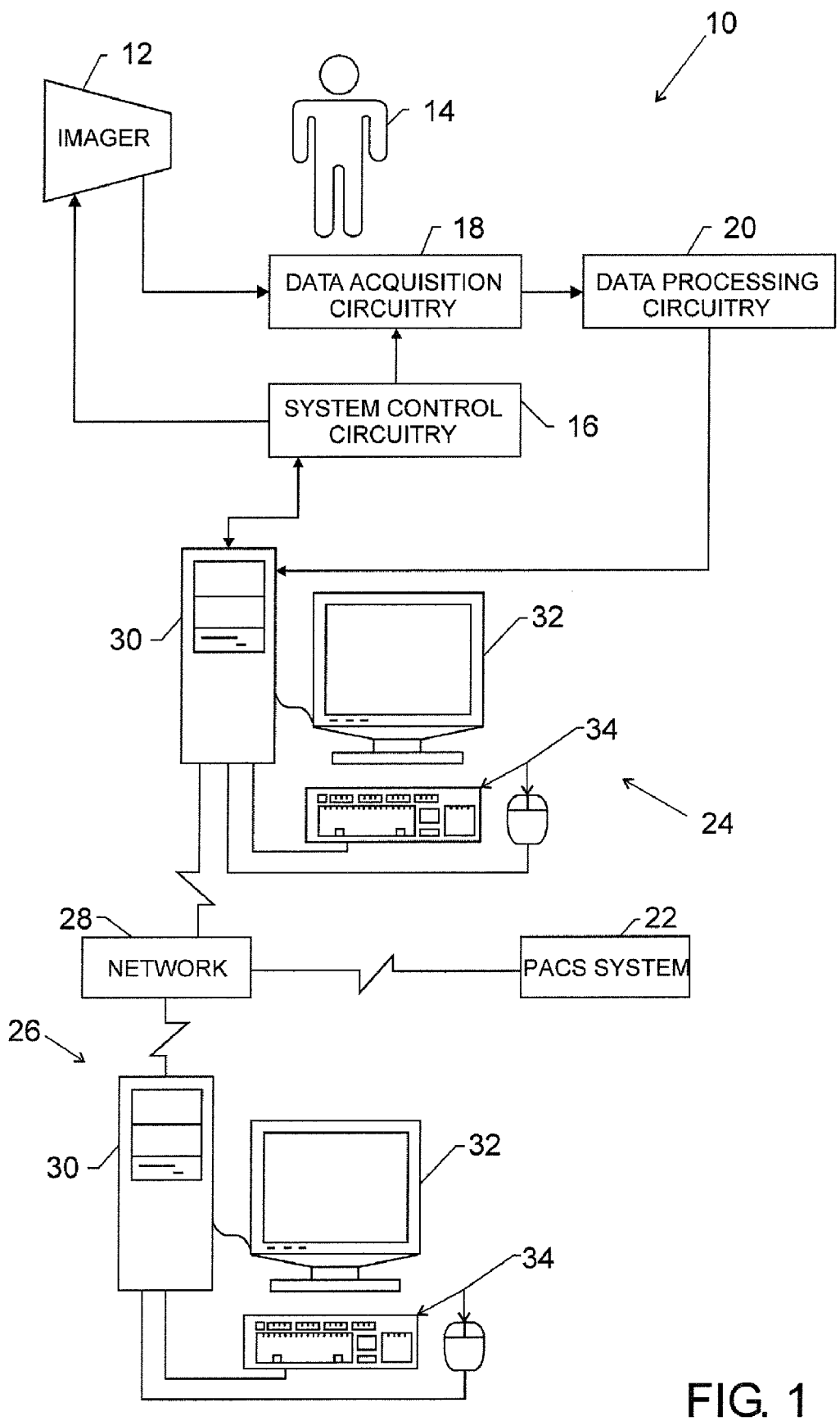
FIG. 1 is a general diagrammatical representation of certain functional components of an exemplary generic imaging system configured for remote operation via the present technique.

Turning now to the drawings, and referring first to FIG. 1, an exemplary collaborative imaging system 10 suitable for use in a medical context is depicted. Generally, the collaborative imaging system 10 includes some type of imager 12 that may operate in accordance with various physical principles for creating image data. In general, the imager 12 creates image data representative of regions of interest in a patient 14 either in a conventional support, such as photographic film, or in a digital medium.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements for storing programs and routines implementing the techniques described herein which may be executed by the system control circuitry 16 or by associated components of the collaborative imaging system 10.

The imager 12, following acquisition of the image data or signals, may process the signals, such as for conversion to digital values, and forward the image data to data acquisition circuitry 18. In the case of analog media, such as photographic film, the data acquisition system may generally include supports for the film, as well as equipment for developing the film and producing hard copies that may be subsequently digitized. For digital systems, the data acquisition circuitry 18 may perform a wide range of initial processing functions, such as adjustment of digital dynamic ranges, smoothing or sharpening of data, as well as compiling of data streams and files, where desired. The data may then be transferred to data processing circuitry 20 where additional processing and analysis are performed. For conventional media such as photographic film, the data processing system may apply textual information to films, as well as attach certain notes or patient-identifying information. For the various digital imaging systems available, the data processing circuitry 20 perform substantial analyses of data, ordering of data, sharpening, smoothing, feature recognition, and so forth, which facilitate the generation of a useful set of image data. The data processing functions may be performed, in general, under the guidance of one or more technologists. The acquired images or image data may be stored in short or long-term storage devices, such as a picture archiving communication system (PACS) 22.

The above-described operations and functions of the collaborative imaging system 10 may be controlled by a scanner console 24, which typically interfaces with the system control circuitry 16. The scanner console 24 may include one or more general purpose or application specific computers 30 or processor-based components. The scanner console 24 may include a monitor 32 or other visual display and one or more input devices 34. The monitor 32 and input devices 34 may be used for viewing and inputting configuration information or for operating aspects of the collaborative imaging system 10, in accordance with the techniques discussed herein. As with the system control circuitry 16, the scanner console 24 may comprise or communicate with a memory or data storage component for storing programs and routines implementing the techniques described herein which may be executed by the scanner console 24 or by associated components of the collaborative imaging system 10. Moreover, the memory or storage component may comprise one or more memory devices, such as magnetic or optical drives, of similar or different types, which may be local or remote from one another.

It should be noted that more than a single scanner console 24 may be provided. For example, an imaging scanner or station may include a console which permits regulation of the parameters involved in the image data acquisition procedure, whereas a different scanner console may be provided for manipulating, enhancing, and viewing resulting reconstructed images.

In addition, a remote console 26 may communicate with other components of the collaborative imaging system 10, such as via a network 28. As will be appreciated by those skilled in the art, any suitable circuitry, such as modems, servers, firewalls, VPN's and so forth may be included within the network 28. For example, the network 28 may include one or more of a local intranet within the medical facility, a service network between the facility and a service provider, a direct communication line between the local and remote components of the collaborative imaging system 10, a virtual private network established over the Internet, the Internet itself, and so forth.

The remote console 26 may comprise many, if not all, of the components of the scanner console 24, such as a monitor 32 and input devices 34. The remote console 26 allows a remote operator to access other elements of the collaborative imaging system 10 via the network 28. For example, the remote console 26 may comprise a PACS workstation or other interface that may be used to access the stored or acquired image data from a remote location. As such, the remote console 26 may be used by a technologist who may assist in the processing of acquired imaging data, a radiologist who reads the acquired or processed imaging data, a referring physician who refers to the analyzed images for patient consultation, and so forth.

In general, the collaborative imaging system 10 provides for collaborative sessions to initiated or joined from the various nodes on the network, such as at the scanner console 24, PACS Server 22, and/or remote consoles 26. In practice, the collaborative environment may be established using various techniques that allow for the concurrent review and/or operation of all or part of a common screen or user interface from each participating node. For example, the software rendering and visualization tools used by the technologist and/or radiologist may be provided to the various participating nodes, allowing operators at those nodes to concurrently view, modify, or process an image data set during the collaborative session. Furthermore, operators at the different nodes joined in a collaborative session may be in communication with one another during the session, such as over a separate voice line, over the network via text-based messaging, or over the network using an audio protocol, such as Voice-over-Internet (VOI). In addition, participants to a collaborative session may attach or share multimedia objects that may be retrieved and/or played by other session participants.

Figure 2:
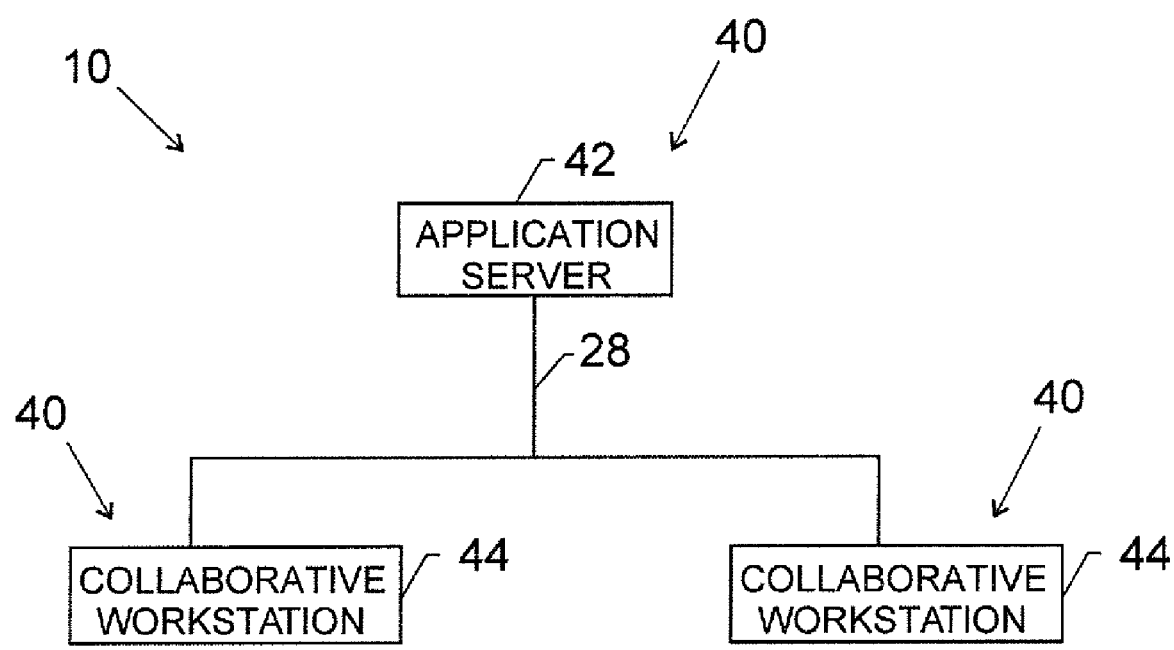
FIG. 2 is a block diagram of certain functional components of a collaborative imaging system in accordance with the present technique.

An exemplary representation of a collaborative network environment is depicted in FIG. 2. As depicted in FIG. 2, a number of participating nodes 40 may be present on a network 28 during a collaborative session. The nodes 40 may be a standalone computer workstation, such as a remote console 26, a scanner console 24, or a PACS server 22. One such node 40 may run an application server 42 routine that enables or runs the collaborative session. The remaining nodes, represented as collaborative workstations 44, may join the session running on the application server via the network 28. When joined to the session, the collaborative workstations 44 may concurrently view all or part of the image data set using software rendering or visualization tools shared through the application server 42.

In one example of a collaborative imaging environment, the application server 42 routine is run on a node that contains an image data set, typically the scanner console 24 or PACS Server 22. The collaborative workstations 44 may be configured as thin clients that may communicate with the application server 42 to initiate, terminate, join, or detach from a collaborative session as desired. As one of ordinary skill in the art will appreciate, multiple collaborative sessions may concurrently exist, depending on the network protocols employed and the available bandwidth. Likewise, the collaborative session may be configured such that collaborative workstations 44 may join or detach from an ongoing collaborative session without disturbing the state of the session. In particular, the collaborative session provides framebuffer communication with sufficient image quality for diagnostic review and analysis at the participating nodes. In one possible implementation of this example, the collaborative imaging environment may be based on the remote framebuffer (RFB) protocol for sharing graphical framebuffers and a multicasting audio connection based on network socket inter-process communication (IPC).

The collaborative workstations 44 may be configured as thin clients to prevent or minimize undesired operator modifications. The thin client configuration may encompass personal computers (PCs) with little or no mass storage capability or with management controls placed on the operating system to prevent local operator alteration. Similarly, the thin client configuration may encompass network computers (NCs), which typically function as a terminal for a mainframe type system, a web browser, and Java engine capable of executing programs or applets written in Java. Other arrangements that may be construed as thin client configurations are possible. Generally, however, a thin client configuration may be construed as one in which the thin client system is not subject to local manipulation or customization by an operator other than to execute one or more programs retrieved from an application or data server.

Because of these types of constraints, collaborative workstations 44 configured as thin clients might load the program or programs to be run from the application server 42. Similarly, changes made at a collaborative workstation 44 might be saved at the application server, presumably the scanner console 24 or PACS system 22. In this manner, the collaborative workstations 44 could have shared concurrent access to the same visualization software and tools as well as to the image data set of interest.

One use of a collaborative imaging system 10 will be discussed with reference to FIG. 1 once again. In particular, a local technologist working at the scanner console 24 may process patients according to a schedule, which may leave insufficient time for the local technologist to post-process the acquired image data using the desired processing routines available on the application server 42. Such post-processing routines may, among other things, process the data into suitable two-dimensional slices or three-dimensional renderings, apply one of more computer assisted detection or diagnosis algorithms, segment features of interest, correct image artifacts, and remove bone or soft tissue.

In the context of a collaborative imaging session, the scanner console 24 or the PACS System 22 may be configured as an application server 42 hosting a collaborative session. One or more remote technologist on respective collaborative workstations 44, such as the remote consoles 26, may then join the session and post-process the acquired image data for a patient, either in conjunction with or instead of the local technologist. The local technologist may then have more available time to process patients. Indeed, the local technologist may focus exclusively on acquiring patient data while remote technologists process the acquired data in either sequential or concurrent sessions. In this manner, the remote technologists may service more than one patient site if desired, with each remote technologist able to provide support as she becomes available to the next patient site requiring assistance.

Furthermore, the local technologist may refer an image data set to an expert in the particular anatomical region or of the particular imaging modality, such as magnetic resonance imaging, mammography, computed tomography, and so forth. In this implementation, problem image data sets or those image data sets outside the expertise of the local technologist may be referred to one or more remote technologists for expert processing. In this manner, expert image processing may be provided without keeping an expert on-site. Conversely, an expert technologist may provide support as a remote expert for more than one imaging site. As noted above, in these implementations, the voice or text communications may be provided between the local and remote technologists, over the network 28 or otherwise, to facilitate concurrent processing, instruction, or interpretation.

In another implementation, a radiologist and referring physician may participate in a collaborative session regarding the patient of the referring physician. For example, referring once again to FIG. 1, the radiologist and referring physician may both use respective remote consoles 26 to join a collaborative session running on an application server, such as on the scanner console 24 or the PACS system 22. During this collaborative session, the radiologist and the referring physician may concurrently review the images and/or volumes using software rendering and/or visualization tools available from the application server 42. In addition, one or more technologists may participate in the collaborative session. In this manner, the radiologist may dynamically convey her diagnosis with appropriate reference to the images when desired. Similarly, the referring physician may ask questions of the radiologist and elicit responsive comments during the collaborative session. The referring physician may thereby obtain a timely and suitably responsive diagnosis, allowing him to appropriately counsel the patient. Furthermore, if desired additional radiologists and/or technologists may join the collaborative session on their respective collaborative workstations 44, such as remote consoles 26, providing additional feedback and/or diagnosis.

While the present technique has been discussed with regard to medical imaging, it may also be applied to other imaging contexts in which the imaging data may be processed and/or analyzed to determine structure or features of interest. For example, security screening, such as baggage, package, or passenger screening, may benefit from the present technique. In the security context, image data may be acquired and reviewed by a screener to determine the presence of illicit material. A collaborative imaging environment may allow local personnel to focus on the flow of passengers or packages during busy periods while remote personnel handle excess or spillover image data. Likewise, equivocal or unclear image data may be reviewed or analyzed by screeners with more experience or specialized knowledge, allowing for the faster and more accurate analysis of the data. As one of ordinary skill in the art will readily apprehend, other imaging contexts and modalities may also benefit from the present technique.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for viewing or manipulating data, comprising:
 establishing a collaborative session, wherein the collaborative session is initiated by an application server at a first node on a network and allows two or more users to concurrently access one or more images from different nodes on the network, wherein the one or more images comprise two-dimensional slices or three-dimensional renderings; and allowing the two or more users to concurrently view and manipulate the one or more images using one or more tools provided by the application server as part of the collaborative session.

2. The method of claim 1, wherein the one or more tools comprise one or more software rendering and visualization tools provided to each user upon joining the collaborative session.

3. The method of claim 1, comprising providing voice or text communication between the two or more users during the collaborative session.

4. The method of claim 1, comprising allowing the users to share one or more multimedia objects via the collaborative session.

5. An image processing system, comprising:
    a primary node configured to run an application server routine that initiates a collaborative session; and
    one or more secondary nodes configured to join the collaborative session via a network;
    wherein the application server routine concurrently provides one or more processing and/or visualization tools to each secondary node joined to the collaborative session such that an image comprising a two-dimensional slice or a volume comprising a three-dimensional rendering may be concurrently viewed and processed at the secondary nodes joined to the collaborative session.

6. The image processing system of claim 5, wherein the primary node comprises a scanner console for an imaging workstation.

7. The image processing system of claim 5, wherein the primary node comprises a picture archiving communication system (PACS) server.

8. The image processing system of claim 5, wherein the one or more secondary nodes comprise at least one workstation remote from the primary node.

9. The image processing system of claim 5, wherein the collaborative session utilizes a remote framebuffer protocol.

10. The image processing system of claim 5, wherein the collaborative session shares graphical framebuffers between the secondary nodes.

11. The image processing system of claim 5, wherein the collaborative session implements a multicast audio connection.

12. A computer readable medium encoding an application server routine comprising:
    code configured to initiate a collaborative session over a network;
    code configured to provide one or more tools from the application server routine to participants of the collaborative session via the network; and
    code configured to allow the participants of the collaborative session to concurrently view and manipulate an image using the one or more tools provided by the application server, wherein the images comprise two-dimensional slices or three-dimensional renderings.

13. The computer readable medium of claim 12, comprising code configured to allow voice or text communication between participants of the collaborative session.

* * * * *